United States Patent [19]
Sillard

[11] Patent Number: 5,927,980
[45] Date of Patent: Jul. 27, 1999

[54] METHOD AND APPARATUS FOR FITTING A FIXED REMOVABLE DENTAL IMPLANT

[76] Inventor: Rannar Sillard, 206 Madison Ave., Lakewood, N.J. 08701

[21] Appl. No.: 09/035,801

[22] Filed: Mar. 6, 1998

Related U.S. Application Data

[60] Provisional application No. 60/043,633, Apr. 14, 1997.
[51] Int. Cl.$^6$ .................................................. A61C 8/00
[52] U.S. Cl. .................................................. 433/173
[58] Field of Search .................................. 433/172, 173, 433/174

[56] References Cited

U.S. PATENT DOCUMENTS

| | | | |
|---|---|---|---|
| 4,931,016 | 6/1990 | Sillard | 433/173 X |
| 5,057,017 | 10/1991 | Sillard | 433/173 X |
| 5,503,557 | 4/1996 | Sillard | 433/172 |

*Primary Examiner*—Nicholas D. Lucchesi
*Attorney, Agent, or Firm*—Clifford G. Frayne

[57] ABSTRACT

A cylindrical bushing interposed between the primary support of a dental implant and a replica of the implant in order to electrically erode the primary support for a secure fit to the replica and hence the implant without causing any electrical erosion to the replica.

4 Claims, 3 Drawing Sheets

METHOD AND APPARATUS FOR FITTING A FIXED REMOVABLE DENTAL IMPLANT

This application claims benefit of Provisional Appln. 60/043,633 filed Apr. 14, 1997.

BACKGROUND OF THE INVENTION

1. Field of Invention

The present invention relates to dental implants and more particularly, relates to a method and apparatus for more accurately fitting the primary support bar and the gold or metal copings secured thereto to the implant fixtures which have been surgically imbedded in the alveolar bone.

2. Description of the Prior Art

In the area of dental prosthetics, there have been primarily two major types of dental implant prosthetics which have been in use. The first, commonly known as the over denture, provides for support structure to be implanted into the alveolar bone which support structure extends above the gum line and permits the patient to snap fit the denture in place. This type of construction permits the patient to remove the denture himself and clean the denture and the gum area. The draw back of the over denture is that it does not normally provide sufficient stability under all eating or chewing conditions.

The second type of prosthesis in wide use is that of the fixed prosthesis. Again a support structure is anchored in the alveolar bone, the support structure extending above the gum line and the prosthesis being permanently secured to the support structure embedded in the bone. This type of prosthesis normally provides a more stable prosthesis for the patient, but aesthetic and hygiene problems arise in that the prosthesis can only be removed by a dentist to permit cleaning of the area under the prosthesis and approximate to the support structure.

U.S. Pat. No. 4,767,328 to Branemark discloses a device for providing such a permanent fixed prosthesis. Further, U.S. Pat. No. 3,748,739 to Thibert, U.S. Pat. No. 4,741,698 to Andrews, U.S. Pat. No. 3,641,671 to Roberts, U.S. Pat. No. 4,085,506 to Lew, and U.S. Pat. No. 3,514,858 to Silverman all disclose versions of permanent or fixed implants. U.S. Pat. No. 4,062,119 to Linkow discloses an implant system for use with removable over dentures.

Applicant has previously developed a dental implant prosthesis which provides for long term stability to the patient, together with the aesthetic appearances required by a dental prosthetic, yet which will permit the patient to remove the prosthesis for cleaning not only the prosthesis, but the gum area surrounding support structures in order to prevent any hygiene problems. This fixed removable dental implant system may be understood with reference to U.S. Pat. No. 4,931,016 and U.S. Pat. No. 5,057,017 to Sillard.

Applicant has continued to refine and develop the methodology utilized in fabricating the fixed removable dental implant system. The methodology relies upon electro discharge machining (EDM) for fabricating the various elements of the dental implant prosthesis as set forth in the aforesaid patents to Sillard.

A persistent problem has been the ability to match the support structure to the implant fixtures which have been embedded in the alveolar bone.

The normal procedure requires the dentist to take an impression of the patient's mouth and this is converted into a master model or actual stone cast of the patient's gum and teeth. After the surgical procedures for embedding or inserting the implant fixtures into the alveolar bone, a similar impression of the patient's gums with the embedded implant fixtures in place is taken and converted into a stone model identifying the location, height, etc., of the implant fixtures. The dental laboratory then replaces portions of the block with actual implant fixtures positioned to the exact height, angle or the like as the implant fixtures which are positioned in the patient's mouth. This fixture which is positioned in the stone model is normally referred to in the industry as the analog or replica in that it is deemed to be an exact replica of the actual implant fixture in the patient's mouth, embedded in the alveolar bone and extending above the gum line. Depending upon whether the dental prosthetic is a complete prosthetic, partial prosthetic, or single tooth prosthetic, there may be one or more implant fixtures positioned within the patient's mouth and hence one or more analogs or replicas positioned in the stone model.

In a full dental prosthetic the support bar which is generally U-shaped in configuration, is designed with a plurality of openings corresponding to the number of implant fixtures embedded in the patient's jaw and the number of analogs or replicas embedded in the stone model. The dental laboratories job is to insure that the support bar makes an accurate fit at each analog or replica location so that when it is fitted into the patient's mouth, there will be an accurate fit with each implant fixture such that when a fastener in the form of a screw is attached through the support bar and into a threaded receptacle in the implant fixture, the support bar will have no wobble within the patient's mouth.

This fitting and fabrication of the support bar in the dental laboratory involves the EDM process between the support bar and the analogs or replicas in the stone model. The exact problem in fabricating the fitting has been that in the EDM process you may be attempting to correct for a very very slight wobble by eroding a small portion of the support bar, but the EDM process may remove or erode material from the analog or replica requiring the dental laboratory technician to repeat the process with respect to all of the analogs or replicas in the stone model in order to obtain the fit desired. In actuality, the actual erosion occurs on the circumferential area on the underside of the support bar surrounding the throughbore for the fastening means. This area is referred to as a gold or metal coping in that it is a gold or metal coping having been secured to the underside of the support bar or fixed bridge or any implant restoration by suitable means (i.e. solder, casting, cement).

Applicant has solved this problem by developing a bushing for positioning between the support bar and the analog or replica during the EDM process which insures that the analog or replica will not be subject to any erosion during the EDM process when making the fitting fabrication between the analog or replica and the support structure. In this manner, the dental technician ensures that the analog or replica in the stone model remains identical to the implant fixture in the patient's mouth. Any excess erosion during the fitting and fabricating process will occur at the bushing and not the analog or replica.

The benefit of this method and the design of the bushing is that it ensures that the support structure fabricated in the laboratory with analogs or replicas will fit in the same manner once it is transferred to the patient's mouth, since the analog or replica and the implant fixture in the patient's mouth will have remained identical during the fabrication process. It can be seen that, if the support bar, in fabricating it to the analogs or replicas in the laboratory differed significantly from its implant fixture counterpart in the patient's mouth, that there could not be an accurate, secure fitting of the support bar in the patient's mouth and further, the patient, after having experienced the surgery once, most surely would not want to have to experience a second oral surgery to implant a new implant fixture.

OBJECTS OF THE INVENTION

It is the object of the present invention to provide for a method for fitting the support bar of a dental implant prosthesis to the implant fixtures embedded in the alveolar bone of the patient's mouth such that there is an accurate, secure fitting which eliminates any wobble or play in the prosthesis.

It is still further object of the present invention to provide for an assembly for fitting the support bar and associated gold or metal copings to the analogs or replicas in the dental laboratory which will ensure that the analogs or replicas are not eroded thus distorting their identity with the actual implant fixture implanted in the patient's alveolar bone.

It is still further object of the present invention to provide for a novel bushing for use in the EDM process which protects the analog or replica from erosion and ensures that it maintains its identity with the implant fixture implanted in the patient's alveolar bone.

SUMMARY OF THE INVENTION

A method and apparatus for fitting a support bar and associated gold coping of a dental implant prosthesis to the actual implant fixtures embedded in the alveolar bone of the patient's mouth, the method and apparatus being performed in the dental laboratory and comprising the positioning of a bushing between the analogs or replicas of the implant fixture embedded in the patient's alveolar bone and the support bar and eroding the gold or metal coping of the support bar to fit and match the analog or replica such than any inadvertent erosion is prevented from effecting the analog or replica and destroying its identity with the implant fixture embedded in the patient's alveolar bone.

BRIEF DESCRIPTION OF THE DRAWINGS

These and other objects of the invention will become evident particularly when taken in light of the following illustrations wherein.

DETAILED DESCRIPTION OF THE DRAWINGS

Figure 1:
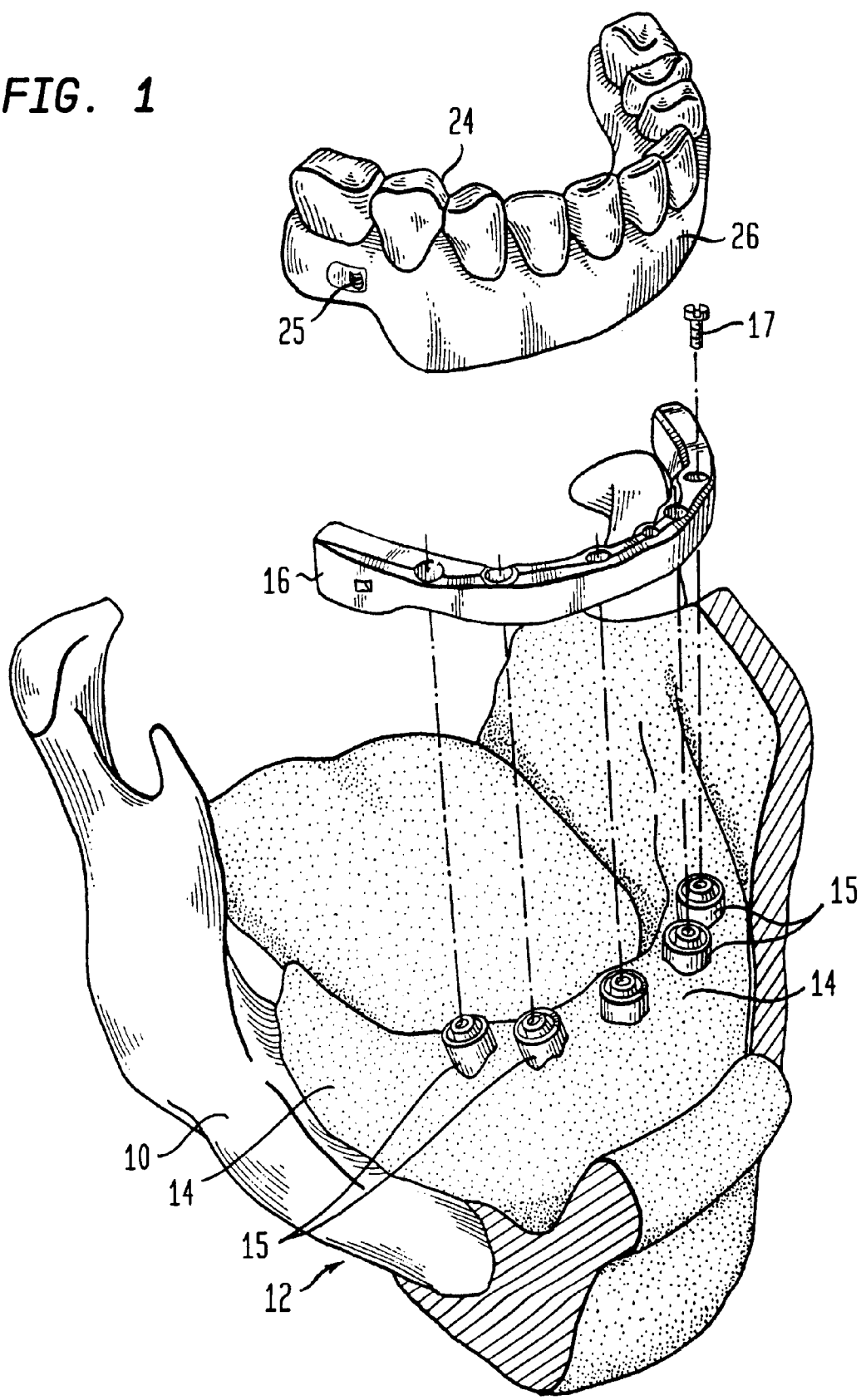
FIG. 1 is an exploded view of a lower jaw with the implant member.
Figure 2A:
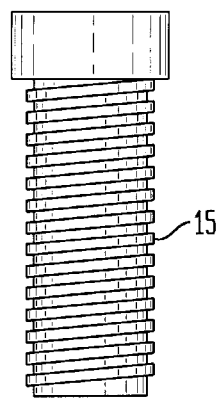
FIG. 2 is a plurality of side views of the implant fixtures.
Figure 2B:
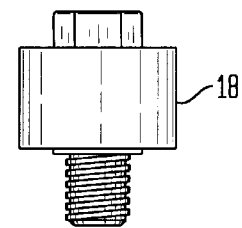
Figure 2D:
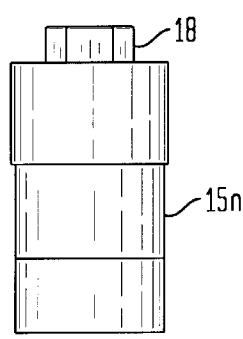
Figure 2C:
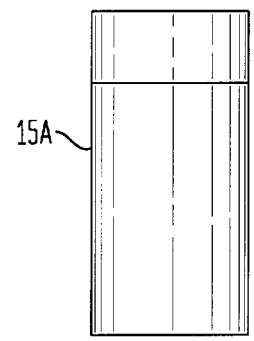

Referring to FIG. 1, there is a prospective, exploded view of a full dental implant for the lower jaw. In FIG. 1, there is illustrated the alveolar bone 10 disposed within the jaw 12 and with the upper portion of the jaw defined by the gum line 14. This lower jaw illustration of a dental implant illustrates a support structure comprising a precision cast bar 16 which is anchored to the alveolar bone 10 by means of a plurality of implant fixtures 15 whose lower ends are threaded and which extend downwardly into the alveolar bone 10. Screws 17 are utilized to secure the precision cast bar 16 to an internally threaded receptacle in the implant fixture.

In the finished product, an acrylic piece 24 and labial flare 26 is secured to the precision cast bar 16 and secured by means of a swivel lock or similar securing device 25.

The dental technician is concerned with the entire fabrication of the full dental prosthesis, but the problem addressed in this application is the fitting of the precision cast bar 16 to the implant fixtures 15 embedded in the alveolar bone 10. To that end, the laboratory technician has the actual precision cast bar 16 and a stone model of the lower jaw of the patient identifying the jaw and gums and identifying the exact location and angularity of the implant fixtures 15 which are actually positioned in the patients mouth. Since the stone model is a replica of the patient's mouth, it is common usage in the trade to refer to the implant fixtures 15 positioned in the stone model as analogs or replicas in that they are identical replicas of the implant fixtures positioned in the patient's mouth including their height, and angularity. We shall therefore reserve the use of the term implant fixtures for those implant fixtures 15 within the patient's mouth and use the term replicas for the fixtures in the stone model.

FIG. 2 is a schematic of generic implant components so that a better understanding of the present invention can be had. FIG. 2A is the actual implant fixture 15 having a threaded body for insertion into the alveolar bone. The upper, non-threaded portion of implant fixture 15 may or may not extend above the gum line depending upon the physiological characteristics of the individual. In the event greater height is required, an abutment 18 illustrated in FIG. 2B is threadedly secured to the internal threaded bore of implant fixture 15. It is to this implant fixture 15 or implant fixture 15 in combination with abutment 18 which the precision bar and gold or metal copings are ultimately secured. FIG. 2C a replica 15A which would be positioned in the stone model and which would present an upper surface identical in height and angularity and shape as the implant fixture 15 in the patient's mouth or the combination of the implant fixture 15 and the abutment 18 within the patient's mouth as illustrated in FIG. 2D.

Figure 3:
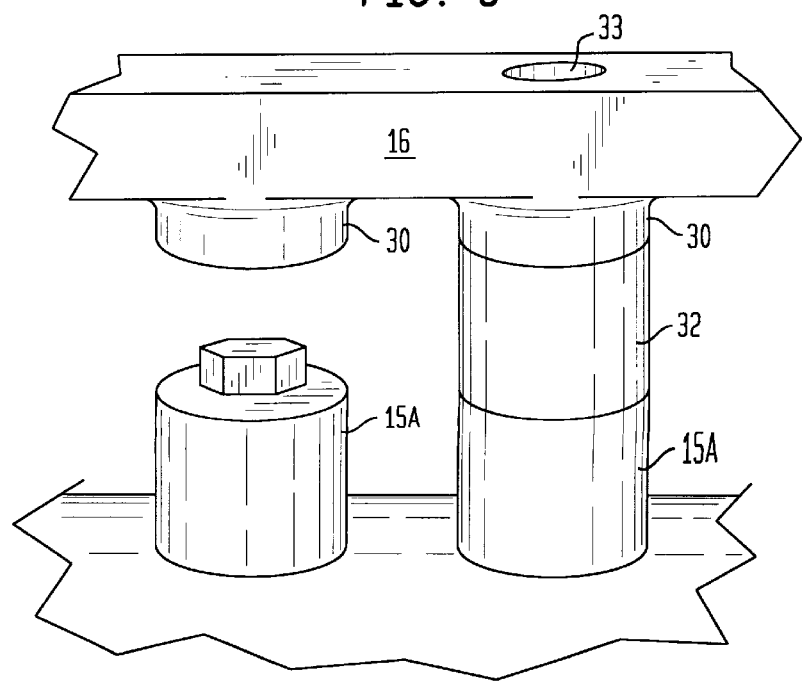
FIG. 3 is a partial side view of the precision cast bar together with replicas associated with the stone model.

FIG. 3 illustrates a partial side view of the relationship between a portion of the precision cast bar 16 and the replica 15A. It will be understood that while the description of the apparatus and process of fitting the precision cast bar to the replica will be set forth respect to the dental technicians manipulations with a stone model 21, that the purpose for this is so that the precision cast bar can be readily transferred from the stone model to the patient's mouth to insure a safe, accurate and firm fit. It should further be understood, that while we are referring to a precision cast bar and a plurality of replicas for a full lower jaw dental prosthetic, the same apparatus and process can be undertaken for a partial dental prosthetic as opposed to a full lower jaw prosthetic and also has application for a single tooth dental implant without departing from the spirit and scope of the invention.

The cast precision bar 16 would have one or more cylindrical protrusions 30 referred to as gold or metal coping depending from the underside of the precision cast bar. Associated with these gold or metal coping 30 would be a throughbore 33 for receipt of screws 17 to secure the precision cast bar to the replica and to the actual implant fixture in the patient's mouth.

Figure 4:
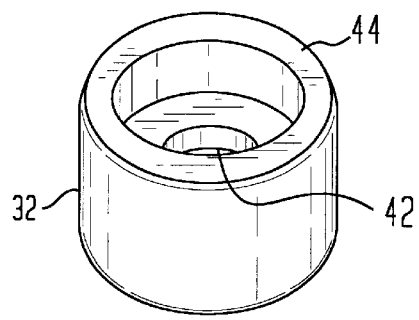
FIG. 4 is a top view of the bushing which is the subject matter of the present invention.
Figure 5:
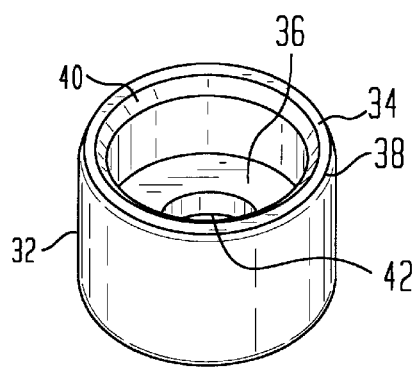
FIG. 5 is a bottom view of the bushing which is the subject of the present invention.

In fitting the precision cast bar 16 to the replica 15A, the cylindrical protrusion, gold or metal coping 30 is eroded by the EDM method utilizing EDM principles to take into account taper, overcut and flux, so that it is configured to the upper surface of the replica 15A which will be identical to the upper surface of implant fixture 15 or implant fixture 15 with abutment. A problem arises in this situation when a portion of the replica 15A suffer erosion during the process. The solution to this problem is the use of a bushing 32 which is interposed between the gold or metal coping 30 on precision cast bar 16 and the replica 15A during the erosion process. FIG. 4 and FIG. 5 are a perspective top view and bottom view respectively of bushing 32. It can be seen in FIG. 5 which is the prospective bottom view of bushing 32 that it comprises a series of concentric recesses 34 and 36 and concentric elevations 38 and 40. It also has a throughbore 42. This underside surface is designed to conform to the upper surface of the replica 15A.

The top perspective view of bushing 32 as illustrated in FIG. 4 illustrates that it has an outer concentric top surface 44 inclined toward the center of the bushing and terminates in a throughbore of 42 which is expanded on the upper surface to permit the head of screw 17 to be recessed. This surface of the bushing will be utilized in the EDM process to erode the outer circumference of the gold or metal coping 30 to conform to the upper surface of replica 15A.

Figure 6:
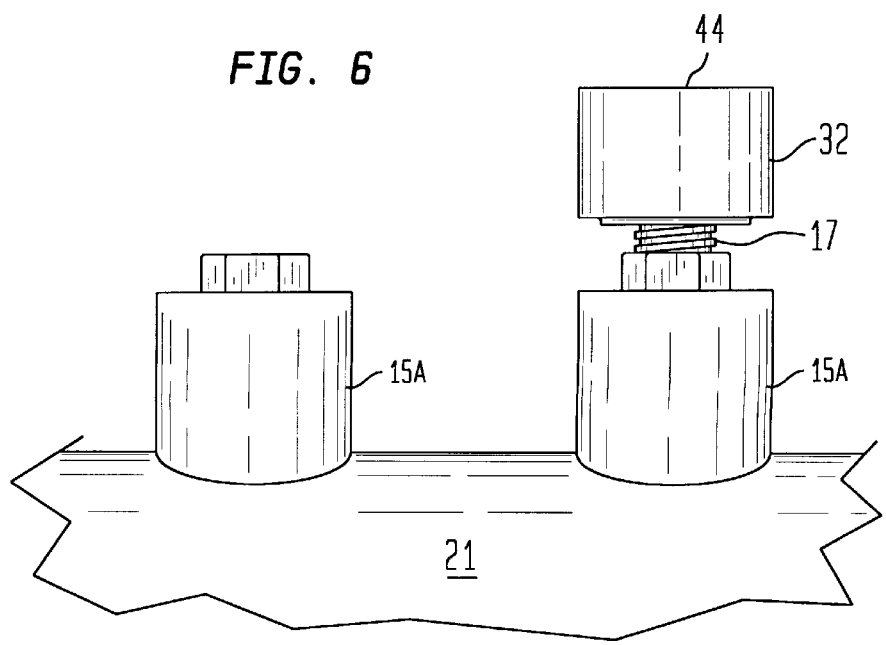
FIG. 6 is a side view illustrating the cooperation between the bushing and the replica in the stone model.

FIG. 6 is a side view of the replica 15A with bushing 32 being secured thereto by screw fastener 17. When fully threaded to the replica 15A, bushing 32 provides an extension of the replica 15A and presents the upper surface 44 as a buffer surface during the EDM process to prevent any erosion of the replicas 15A.

In this configuration, the precision cast bar and the stone block with bushings positioned between the replicas and the precision cast bar 16 would be emerged in a dielectric bath for application of the EDM process as described in the aforementioned Sillard patents and made part hereof. Utilizing this protocol with a bushing 32 designed in accordance with the description herein, assures an accurate erosion of the depending gold or metal coping 30 of precision cast bar 16 and eliminates the possibility of any erosion of the replica 15A. At the conclusion of the process, the bushing would be removed from the replica 15A and the gold or metal coping 30 of precision cast bar 16 would be secured directly to the replica 15A using fastening means 17 to check for fit and the absence of play or wobble. Using this process, if the precision cast bar 16 is secured to the replica 15A without play or wobble, the technician is assured that the precision cast bar will fit in the same manner to the actual implant fixture 15 secured within the patient's mouth.

I claim:

1. An apparatus for accurately fitting the primary support of a dental implant to the abutment or implant support positioned in the alveolar bone of the individual, the apparatus utilized in the dental laboratory with a replica of said abutment or implant, said apparatus comprising:

a cylindrical bushing having an upper surface and a lower surface and a centrally disposed throughbore therethrough, said lower surface of said bushing having a surface complimentary with the upper surface of the replica, said upper surface of said bushing having a surface identical to said upper to be surface of said replica, said bushing adapted to be secured to said replica by means of a screw through said throughbore, said bushing and a depending cylinder of said primary support having been subjected to an electrical discharge method to erode said depending cylinder surface to conform to the upper surface of said replica, without eroding said upper surface of said replica.

2. The cylindrical bushing in accordance with claim 1 wherein said diameter of said cylindrical bushing is greater than the diameter of said depending cylinder of said primary support.

3. The cylindrical bushing in accordance with claim 1 wherein said bushing is fabricated out of a suitable conductive alloy.

4. An improved process for the fabrication and fitting of a primary support bar of a dental implant to an implant support secured in the alveolar bone of an individual, wherein a master cast is prepared of the patient's mouth with implants in place, replicas of said implants are positioned in said master cast in the identical position of said implants in said patient's mouth, and said primary support bar is fitted to said replicas by means of an electrical discharge method, the improvement in the process for fitting and fabricating comprising:

a. preparing a cylindrical bushing having an upper surface and a lower surface, said lower surface complimentary with the upper surface of said replica and an implant and said upper surface of said bushing being identical to said upper surface of said replica and an implant;

b. securing said cylindrical bushing to said replica;

c. connecting said primary support bar to a first electrode and submersing said primary support bar in a mineral oil or dilectium bath;

d. connecting said replica and said cylindrical bushing to a second electrode of opposing charge and submerging in said mineral oil or dilectium bath;

e. gradually bringing said primary support bar and said cylindrical bushing into contact under the influence of electrical discharge erosion;

f. eroding a complimentary surface on said primary support bar complimentary to said upper surface of said replica preventing any erosion from occurring on said replica;

g. removing said support bar and said replica from said mineral oil or dilectium bath and checking the fit between said primary support bar and said upper surface of said replica;

h. repeating steps e through g as required to obtain secure fit.

\* \* \* \* \*